(12) United States Patent
Ferrante et al.

(10) Patent No.: US 8,308,340 B2
(45) Date of Patent: Nov. 13, 2012

(54) COMPOSITE MIXER

(75) Inventors: Joseph M. Ferrante, Bartlett, TN (US); Si Janna, Memphis, TN (US); Thomas Mayr, Hudson, WI (US); Jeremy Odegard, River Falls, WI (US); Wayne Phillips, Hudson, WI (US); David Schuelke, Hudson, WI (US)

(73) Assignee: Smith & Nephew, Inc., Memphis, TN (US)

( * ) Notice: Subject to any disclaimer, the term of this patent is extended or adjusted under 35 U.S.C. 154(b) by 916 days.

(21) Appl. No.: 11/791,255

(22) PCT Filed: Nov. 22, 2005

(86) PCT No.: PCT/US2005/042594
§ 371 (c)(1),
(2), (4) Date: May 1, 2008

(87) PCT Pub. No.: WO2006/058153
PCT Pub. Date: Jun. 1, 2006

(65) Prior Publication Data
US 2008/0316855 A1    Dec. 25, 2008

Related U.S. Application Data

(60) Provisional application No. 60/630,463, filed on Nov. 23, 2004.

(51) Int. Cl.
*B01F 5/06* (2006.01)
(52) U.S. Cl. .................. 366/162.3; 366/181.5; 366/341; 222/137; 222/145.6

(58) Field of Classification Search .................... 138/42; 222/135, 145.6, 459, 137; 366/158.5, 181.5, 366/336–341, 162.3
See application file for complete search history.

(56) References Cited

U.S. PATENT DOCUMENTS

| | | | | |
|---|---|---|---|---|
| 835,619 A * | 11/1906 | Issacs et al. | ................. | 366/165.4 |
| 1,024,688 A * | 4/1912 | Lewis | ............. | 181/272 |
| 1,711,270 A * | 4/1929 | Litle, Jr. | ........... | 138/42 |
| 1,977,300 A * | 10/1934 | Blunt | ............. | 366/336 |
| 2,856,962 A * | 10/1958 | Christoph | ........... | 138/42 |
| 3,330,444 A * | 7/1967 | Raypholtz | ............ | 222/137 |
| 3,358,749 A * | 12/1967 | Chisholm et al. | ............. | 165/141 |
| 3,361,412 A * | 1/1968 | Cole, III | ......... | 366/268 |
| 3,450,022 A * | 6/1969 | Engel | ............... | 99/453 |
| 3,460,809 A * | 8/1969 | Hauss | ............. | 366/338 |
| 3,554,256 A | 1/1971 | Anderson | | |
| 3,623,704 A * | 11/1971 | Skobel | ........ | 366/160.1 |

(Continued)

FOREIGN PATENT DOCUMENTS
EP                00528208             2/1996
(Continued)

OTHER PUBLICATIONS

Osteoset® Injector, Wright Medical Technology, Inc. Bio-Orthopaedics Group, 02 pages (1999).

(Continued)

*Primary Examiner* — David Sorkin
(74) *Attorney, Agent, or Firm* — Kilpatrick Townsend & Stockton LLP

(57) ABSTRACT

Devices and methods for mixing a clotting agent with other inputs such as blood, blood derived product, bone marrow, and/or bone marrow derived product to form a congealed mixture.

20 Claims, 3 Drawing Sheets

U.S. PATENT DOCUMENTS

| | | |
|---|---|---|
| 3,685,248 A | 8/1972 | Godelaine |
| 3,874,643 A * | 4/1975 | Lorenian et al. ............ 366/76.92 |
| 3,934,824 A * | 1/1976 | Fitzhugh ................... 239/533.13 |
| 3,941,350 A * | 3/1976 | Kluczynski ..................... 251/127 |
| 3,941,355 A * | 3/1976 | Simpson ......................... 366/99 |
| 3,965,975 A * | 6/1976 | Edmundson .................. 165/108 |
| 4,109,653 A | 8/1978 | Kozam et al. |
| 4,141,864 A | 2/1979 | Rijke et al. |
| 4,316,673 A * | 2/1982 | Speer ............................. 366/337 |
| 4,405,249 A | 9/1983 | Scales |
| 4,471,765 A | 9/1984 | Strauss et al. |
| 4,485,096 A | 11/1984 | Bell |
| 4,485,097 A | 11/1984 | Bell |
| 4,538,920 A * | 9/1985 | Drake ......................... 366/181.5 |
| 4,551,135 A | 11/1985 | Gorman et al. |
| 4,594,005 A * | 6/1986 | Sakamoto et al. .......... 366/181.5 |
| 4,631,055 A | 12/1986 | Redl et al. |
| 4,632,672 A | 12/1986 | Kvitrud |
| 4,668,097 A * | 5/1987 | Nygren et al. .............. 366/162.3 |
| 4,735,616 A | 4/1988 | Eibl et al. |
| 4,753,536 A * | 6/1988 | Spehar et al. .................. 366/339 |
| 4,767,026 A * | 8/1988 | Keller et al. ................... 222/137 |
| 4,769,011 A | 9/1988 | Swaniger |
| 4,776,704 A * | 10/1988 | Kopunek et al. ............... 366/184 |
| 4,820,306 A | 4/1989 | Gorman et al. |
| 4,856,567 A | 8/1989 | Cosmai |
| 4,861,165 A * | 8/1989 | Fredriksson et al. ....... 366/165.1 |
| 4,874,368 A | 10/1989 | Miller et al. |
| 4,917,702 A | 4/1990 | Scheicher et al. |
| 4,964,733 A * | 10/1990 | Fredriksson et al. .......... 366/336 |
| 4,978,336 A | 12/1990 | Capozzi et al. |
| 4,994,065 A | 2/1991 | Gibbs et al. |
| 5,033,650 A * | 7/1991 | Colin et al. .................... 222/137 |
| 5,073,373 A | 12/1991 | O'Leary et al. |
| 5,078,699 A | 1/1992 | Haber et al. |
| 5,080,262 A * | 1/1992 | Herold et al. .................. 222/135 |
| 5,104,375 A | 4/1992 | Wolf et al. |
| 5,116,315 A | 5/1992 | Capozzi et al. |
| 5,122,116 A | 6/1992 | Kriesel et al. |
| 5,125,913 A * | 6/1992 | Quackenbush ................ 604/264 |
| 5,133,755 A | 7/1992 | Brekke |
| 5,152,763 A | 10/1992 | Johnson |
| 5,174,316 A * | 12/1992 | Keller et al. ................ 134/104.3 |
| 5,181,918 A | 1/1993 | Brandhorst et al. |
| 5,185,001 A | 2/1993 | Galanakis |
| 5,190,524 A | 3/1993 | Wex |
| 5,190,525 A | 3/1993 | Oswald et al. |
| 5,232,437 A | 8/1993 | Lysaght et al. |
| 5,286,258 A | 2/1994 | Haber et al. |
| 5,290,552 A | 3/1994 | Sierra et al. |
| 5,314,412 A | 5/1994 | Rex |
| 5,314,476 A | 5/1994 | Prewett et al. |
| 5,329,976 A | 7/1994 | Haber et al. |
| 5,332,313 A * | 7/1994 | Cimbalik et al. ............. 366/303 |
| 5,366,507 A | 11/1994 | Sottosanti |
| 5,366,508 A | 11/1994 | Brekke |
| 5,368,563 A | 11/1994 | Lonneman et al. |
| 5,413,253 A * | 5/1995 | Simmen ....................... 222/137 |
| 5,445,614 A | 8/1995 | Haber et al. |
| 5,464,439 A | 11/1995 | Gendler |
| 5,496,473 A | 3/1996 | Chow |
| 5,510,396 A | 4/1996 | Prewett et al. |
| 5,516,209 A * | 5/1996 | Flint et al. ..................... 366/340 |
| 5,540,849 A * | 7/1996 | Dugan ........................... 210/767 |
| 5,577,517 A | 11/1996 | Bonutti |
| 5,585,007 A | 12/1996 | Antanavich et al. |
| 5,586,821 A | 12/1996 | Bonitati et al. |
| 5,591,232 A | 1/1997 | Rahimi et al. |
| 5,632,906 A | 5/1997 | Ishida |
| 5,674,394 A | 10/1997 | Whitmore |
| 5,683,406 A | 11/1997 | Altobelli et al. |
| 5,683,459 A | 11/1997 | Brekke |
| 5,694,951 A | 12/1997 | Bonutti |
| 5,697,932 A | 12/1997 | Smith et al. |
| 5,718,707 A | 2/1998 | Mikhail |
| 5,733,545 A | 3/1998 | Hood, III |
| 5,755,792 A | 5/1998 | Brekke |
| 5,772,665 A | 6/1998 | Glad et al. |
| 5,824,084 A | 10/1998 | Muschler |
| 5,863,296 A | 1/1999 | Orton |
| 5,863,297 A | 1/1999 | Walter et al. |
| 5,865,797 A | 2/1999 | Zeeman |
| 5,881,536 A | 3/1999 | Muller-Wille et al. |
| 5,901,883 A | 5/1999 | Ritsche |
| 5,911,252 A | 6/1999 | Cassel |
| 5,925,051 A | 7/1999 | Mikhail |
| 5,935,437 A | 8/1999 | Whitmore |
| 5,997,811 A | 12/1999 | Esposito |
| 6,001,259 A | 12/1999 | Whitmore |
| 6,010,627 A | 1/2000 | Hood, III et al. |
| 6,019,765 A | 2/2000 | Thornhill et al. |
| 6,045,555 A | 4/2000 | Smith et al. |
| 6,049,026 A | 4/2000 | Muschler |
| 6,062,722 A * | 5/2000 | Lake ............................. 366/130 |
| 6,109,895 A | 8/2000 | Ray |
| 6,132,396 A | 10/2000 | Antanavich et al. |
| 6,153,104 A | 11/2000 | Robertson |
| 6,203,296 B1 | 3/2001 | Ray |
| 6,203,573 B1 | 3/2001 | Walter et al. |
| 6,251,098 B1 | 6/2001 | Rake |
| 6,274,090 B1 | 8/2001 | Coelho et al. |
| 6,296,667 B1 | 10/2001 | Johnson et al. |
| 6,302,574 B1 * | 10/2001 | Chan ........................... 366/160.4 |
| 6,311,690 B1 | 11/2001 | Jefferies |
| 6,315,795 B1 | 11/2001 | Scarborough et al. |
| 6,326,018 B1 | 12/2001 | Gertzman |
| 6,342,157 B1 | 1/2002 | Hood, III et al. |
| 6,379,035 B1 * | 4/2002 | Kubo et al. .................... 366/340 |
| 6,379,340 B1 | 4/2002 | Zinger et al. |
| 6,394,314 B1 * | 5/2002 | Sawhney et al. ............... 222/137 |
| 6,398,972 B1 | 6/2002 | Blasetti |
| 6,402,364 B1 * | 6/2002 | Esclar et al. ................ 366/160.4 |
| 6,409,972 B1 * | 6/2002 | Chan ............................. 422/131 |
| 6,461,325 B1 | 10/2002 | Delmotte et al. |
| 6,472,162 B1 | 10/2002 | Coelho et al. |
| 6,475,183 B1 | 11/2002 | Epstein et al. |
| 6,488,650 B1 | 12/2002 | Epstein et al. |
| 6,544,751 B1 | 4/2003 | Brandwein et al. |
| 6,626,329 B2 | 9/2003 | Rake |
| 6,629,947 B1 | 10/2003 | Sahatjian et al. |
| 6,644,365 B1 | 11/2003 | Spero et al. |
| 6,659,982 B2 | 12/2003 | Douglas |
| 6,679,300 B1 | 1/2004 | Sommer et al. |
| 6,685,923 B2 | 2/2004 | Peterson et al. |
| 6,723,067 B2 | 4/2004 | Nielson |
| 6,764,467 B1 | 7/2004 | Roby et al. |
| 6,884,230 B1 | 4/2005 | Epstein et al. |
| 7,056,738 B2 | 6/2006 | Prockop et al. |
| 7,077,146 B1 | 7/2006 | Eckerson |
| 7,077,176 B2 | 7/2006 | Py |
| 7,081,103 B2 | 7/2006 | Epstein et al. |
| 7,141,054 B2 | 11/2006 | Vandewalle |
| 7,175,336 B2 | 2/2007 | Voellmicke et al. |
| 7,179,391 B2 | 2/2007 | Leach et al. |
| 7,291,450 B2 | 11/2007 | Sowemimo-Coker et al. |
| 7,803,141 B2 * | 9/2010 | Epstein et al. ................. 604/264 |
| 2001/0037079 A1 | 11/2001 | Burban |
| 2001/0043940 A1 | 11/2001 | Boyce et al. |
| 2001/0053547 A1 | 12/2001 | Slichter |
| 2002/0123735 A1 | 9/2002 | Rake |
| 2002/0127720 A1 | 9/2002 | Erbe et al. |
| 2002/0179537 A1 | 12/2002 | Sukavaneshvar et al. |
| 2002/0191487 A1 | 12/2002 | Sand |
| 2003/0044322 A1 * | 3/2003 | Andersson et al. ........... 422/100 |
| 2003/0230521 A1 | 12/2003 | Schick |
| 2003/0233067 A1 | 12/2003 | McIntosh et al. |
| 2004/0071668 A1 | 4/2004 | Bays et al. |
| 2004/0108333 A1 | 6/2004 | Rake |
| 2004/0167617 A1 | 8/2004 | Voellmicke et al. |
| 2004/0193071 A1 | 9/2004 | Binette et al. |
| 2005/0078553 A1 * | 4/2005 | Wilken ......................... 366/336 |
| 2006/0051448 A1 * | 3/2006 | Schryver et al. .............. 425/381 |
| 2006/0064070 A1 | 3/2006 | Martin |
| 2008/0081033 A1 | 4/2008 | Sowemimo-Coker |
| 2008/0081367 A1 | 4/2008 | Sowemimo-Coker |
| 2008/0304355 A1 | 12/2008 | Sattig et al. |

FOREIGN PATENT DOCUMENTS

| | | |
|---|---|---|
| EP | 0 747 114 A1 | 12/1996 |
| EP | 0928617 | 7/1999 |
| EP | 00664717 | 4/2001 |
| EP | 00578086 | 8/2001 |
| EP | 0 116 6818 | 1/2002 |
| EP | 1462059 A | 9/2004 |
| EP | 1466572 A2 | 10/2004 |
| JP | 60087838 A * | 5/1985 |
| JP | 06343698 | 12/1994 |
| WO | WO 84/00340 | 2/1984 |
| WO | WO 93/14797 | 8/1993 |
| WO | WO 96/27397 | 9/1996 |
| WO | WO 97/34651 | 9/1997 |
| WO | WO 98/10807 | 3/1998 |
| WO | WO 98/11349 | 3/1998 |
| WO | WO 98/11350 | 3/1998 |
| WO | WO 98/35710 | 8/1998 |
| WO | WO 99/67015 | 12/1999 |
| WO | WO 00/61256 | 10/2000 |
| WO | WO 00/62840 | 10/2000 |
| WO | WO 01/62333 | 8/2001 |
| WO | WO 01/72369 | 10/2001 |
| WO | WO 01/85233 | 11/2001 |
| WO | WO 02/40963 | 5/2002 |
| WO | WO 02/058762 | 8/2002 |
| WO | WO 02/058762 A2 | 8/2002 |
| WO | WO 02/067867 | 9/2002 |
| WO | WO 02/089737 | 11/2002 |
| WO | WO 03/090683 | 11/2003 |
| WO | WO 2004/004802 | 1/2004 |
| WO | WO 2004/108060 A1 | 12/2004 |
| WO | WO 2004/108533 | 12/2004 |
| WO | WO 2005/094914 | 10/2005 |
| WO | WO 2006/058153 | 6/2006 |

OTHER PUBLICATIONS

Osteoset® Bone Graft Substitute Surgical Grade Calcium Sulfate, 04 pages (2000).

Orthovita Products: Imbibe Bone Marrow Aspiration Syringe, 03 pages (2004) http://www.orthovita.com/products/vitoss/imbibe.html.

Hip implants, knee implants, biologic products, bone graft substitutes—Wright Medical, 02 pages (2004) http://www.wmt.com/Physicians/Products/Biologics/CELLPLEXTCPSyntheticCancellousBone.asp.

Shulman, et al., 'Augmented Autologous Transfusions in Major Reconstructive Spine Surgery,' *J. Clin. Apheresis*, 1362-8 (1998).

Bolan, et al., 'Transfusion Medicine Management for Reconstructive Spinal Repair in a Patient with von Willebrand's Disease and a History of Heavy Surgical Bleeding,' *Spine*, 26(23):E552-6 (Dec. 2001).

Piston Syringe, 510(k) Notification, Orthovita, Inc. 510(k) Summary Piston Syringe, 05 pages (2001).

Platelet Richard Plasma Products, 04 pages (2004) Harvest® Developing technologies for accelerating healing, naturally™, http://www.harvesttech.com/Global/Global_Disposables_APC.htm.

U.S. Appl. No. 11/868,008, filed Oct. 5, 2007, Sowemimo-Coker, et al.

U.S. Appl. No. 11/868,093, filed Oct. 5, 2007, Sowemimo-Coker, et al.

Blazsek, et al., 'Large scale recovery characterization of stromal cell-associated primitive haemopoietic progenio cells from filtger-retained human bone marrow,' *Bone Marrow Transplantation* 23:647-657 (1999).

Merriam-Webster Medical Dictionary online, 'solution,' accessed Sep. 19, 2006.

Connolly, John, et al., 'Development of an Osteogenic Bone-Marrow Preparation,' *Journal of Bone and Joint Surgery* (Jun. 5, 1989), vol. 71-A, pp. 684-691.

Surgical Autologous Growth Factor Extracts, Nov. 28, 2000, pp. 1-14.

Eichler, et al., 'Engraftment Capacity of Umbilical Cord Blood Cells Processed by Either Whole Blood Preparation or Filtration'; *Stem Cells*; 2003; pp. 208-216; vol. 21.

Lee, et al., 'Wintrobe's Clinical Hematoloy'; book; 10$^{th}$ edition; Jan. 15, 1999; pp. 1124-1126 and p. 2741; Lippincott Williams & Wilkins; vol. 2; Philadelphia; Baltimore; New York; London; Buenos Aires; Hong Kong; Sydney; Tokyo.

Lucarelli, et al., 'Platelet-derived growth factors enhance proliferation of human stromal stem cells'; Biomaterials; Aug. 2003; 3095-100; vol. 24(18).

Niyibizi, et al., 'Novel approaches to fracture healing'; Expert Opinion on Investigational Drugs; Jul. 2000; pp. 1573-1580; vol. 9(7).

Takigami, et al.; 'Spine Fusion Using Allograft Bone Matrix Enriched in Bone Marrow Cells and Connective Tissue Progenitors'; 48$^{th}$ Annual Meeting of the Orthopedic Research Society; The Spine Journal; Sep. 2002; pp. 100; vol. 2(5).

The ABC's of Filtration Bioprocessing for the Third Millennium, book; Pall Corporation; 2002; Northern Boulevard, East Hills, NY 11548, pp. 1-13 SPECTRUMLABS.COM.

GPS® III System, 'Leadership through Technology,' GPS® III Platelet Separation System, Biomet® Biologics, 08 pages (2007).

GPS® III System, 'the new Gold Standard,' GPS® II Platelet Concentrate System, Biomet® Biologics, 14 pages (2006).

Plasmax™ Plasmax Concentrate, Biomet® Biologics, Inc., 06 pages (2006).

GPS® II System, 'the new Gold Standard,' GPS® II Platelet Concentrate System, (FT Cell Factor Technologies, Inc., a Biomet Company, 10 pages (2004).

Operative Technique, Smith & Nephew CAPTION Disposable Platelet Concentrator, 16 pages (2007).

DePuySpine™ a Johnson & Johnson Company, Symphony™ II Platelet Concentrate System, 01 page (Mar. 6, 2008) http://www.depuyspine.com/products/biologicsolutions/ii.asp.

DePuySpine™ a Johnson & Johnson Company, Symphony™ Platelet Concentrate System, 01 page (Mar. 6, 2008) http://www.depuyspine.com/products/biologicsolutions/pcs.asp.

Redi-Flow Filter® Suction System, Information for Medical Professionals, 03 pages (Mar. 6, 2008) http://www.biomet.com/hcp/prodpage.cfm?c=0E&p=090402.

Biomet Biologics, Inc., featuring the GPS System, 01 page (Mar. 6, 2008) http://www.biometbiologics.com/.

Biomet Biologics, Inc.: What is Platelet Concentrate? 02 pages (Mar. 6, 2008) http://www.biomebiologics.com/whatis.cfm.

Biomet Biologics, Inc.: GPS™ System Advantages, 02 pages (Mar. 6, 2008) http://www.biometbiologics.com/whygps.cfm.

Tamari, et al., Perfusion, 14:453-9 (1999).

* cited by examiner

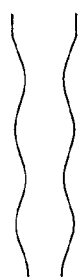  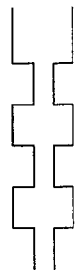  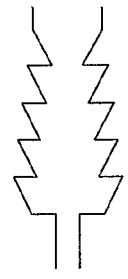
FIG. 5A   FIG. 5B   FIG. 5C   FIG. 5D   FIG. 5E
   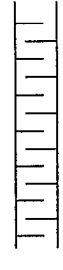 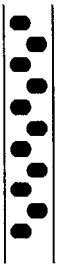
FIG. 6A   FIG. 6B   FIG. 6C   FIG. 6D   FIG. 6E
FIG. 7
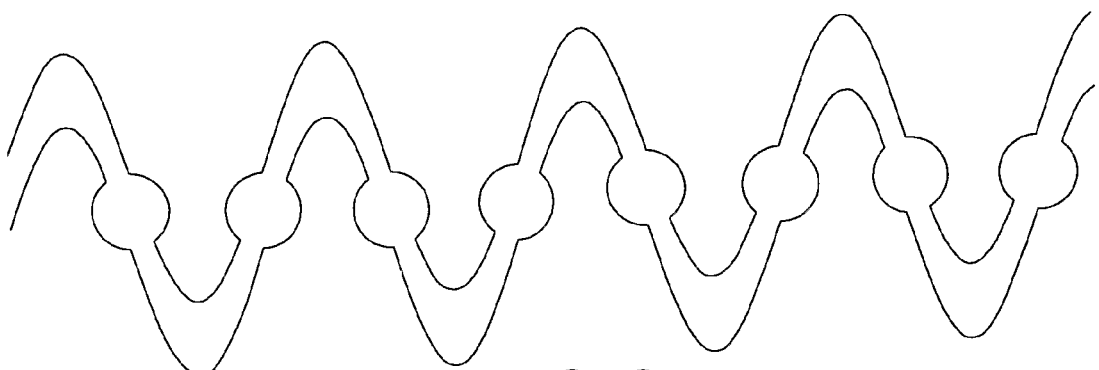
FIG. 8

COMPOSITE MIXER

RELATED APPLICATIONS

This application is the U.S. national phase application of International Application No. PCT/US2005/042594 filed Nov. 22, 2005, and published in English on Jun. 1, 2006 as International Publication No. WO 2006/058153 A1, which claims the benefit of U.S. Provisional Patent Application Ser. No. 60/630,463, entitled "Composite Mixer" filed Nov. 23, 2004, the entire contents of which are hereby incorporated by this reference.

RELATED FIELDS

Embodiments of the present invention relate to methods and devices for mixing a clotting agent with one or more other inputs to form a congealed mixture.

BACKGROUND

Bone voids and non-unions are often the result of trauma, fracture, tumor removal, or surgical implant procedures such as total joint replacement. Bone voids and non-unions are treated in a variety of ways. In many cases, surgeons take filler and apply it at the site of the bone void or non-union to fill in gaps and help the bone grow. This filler may be or include constituents from the patient's own body, a donor's body, or another species' body, as well as other naturally occurring and synthetic substances. The filler is typically a mixture of a clotting agent with blood platelets and/or bone graft. Some people believe that blood platelets facilitate the healing of bone and other tissue and that bone graft and similar substances provide useful scaffolding for new bone to grow around.

In some surgical procedures, blood is taken from the patient and used to create a platelet rich concentration by separating out the platelets from other components of the blood. The platelet rich concentrate is then mixed with one or more clotting agents, such as thrombin, collagen (e.g. gelfoam, microfibrillar collagen), calcium salts (e.g. calcium chloride), gelatin paste or foam, fibrin glue, bone wax, epinephrine, and/or oxidized cellulose, which facilitate congealing. Thrombin, for example, breaks down some of the blood components and causes them to interdigitate or weave themselves together. After a short period of time, the mixture congeals and may be used to treat a bone fracture, a non-union area, or a bone void. The presence of blood platelets may help the patient heal or heal faster then he or she otherwise would. The area filled in may eventually turn back into bone. Note that the use of the platelet rich mixture is not limited to filling bones. Such mixtures are thought to have healing benefits for other tissue types as well. For example, a tissue wound such as a burn may benefit from treatment with a platelet rich mixture. The mixture may be applied to help the skin reform. A variety of other uses are possible.

In the case of bone voids and non-unions, the filler may contain a scaffolding substance, such as bone graft, that provides a scaffold for new bone to grow around. Bone graft is morcelized or crumbled up bone and may come from a donor (allogenic), the patient's own bones (autologous), or from another species' bones (xenologous). In addition to naturally derived bone graft, a synthetic substance such as a resorbable polymer may be used as a scaffolding substance. Ceramics such as calcium phosphate, calcium sulfate, or silicon oxide may be used. The scaffolding substances may be any combination of osteoconductive, osteoinductive, or biocompatible materials.

Generally, a filler mixture is composed of a clotting agent and one or more of blood, blood derived product, bone marrow, or bone marrow derived product. Thus, for example, filler may be a mixture of a clotting agent, a scaffolding substance, and a platelet rich concentrate. Such filler might be used in a bone graft procedure in which the filler is inserted into a bone void to provide an environment for and induce new bone growth. The mixture may include a variety of other inputs like proteins, angiogenic factors, osteogenic factors, antibacterial agents, drugs, pain medication, and/or any other suitable medically beneficial input.

The mixture of clotting agent with other input constituents or materials is often performed at or around the time of the surgical procedure in which the mixture is used. In some cases, this is because the use-ability and ease of handling of the congealed mixture begins to decrease after the mixture has congealed for an hour or so, when it begins to shrink and secrete liquid. For a relatively short period of time after congealing, the mixture is typically easier to handle because it can be easily cut and shaped. After congealing for five hours, many mixtures will have become unusable. In addition, when inputs from the mixture come from the patient (e.g., blood platelets), it is often convenient to obtain those inputs from the patient at or around the time of surgery rather than long before. Generally, within a minute or a minute and a half of mixing, the mixture congeals into a useable substance that is good for up to around five hours.

There are a variety of ways to mix the clotting agent with the other input or inputs. For example, the surgeon may make the mixture by adding the ingredients to a small dish or bowl and mixing them. As another example, the materials may be placed together into a syringe as in U.S. patent application 2002/0127720 to Erbe et al., which is incorporated herein by this reference. Erbe et al. describe a syringe for bone marrow aspirate and other biocompatible materials in which mixing can occur. However, there is potential for the constituents not to mix as desired.

Similarly, there is, among other things, potential for the constituents to not interact as desired in the Depuy Symphony Graft Delivery System, which allows two liquids to enter a conveyance device where they interact. The end user may or may not be successful at facilitating sufficient interaction and mixing with manual agitations such as by shaking the container. U.S. Patent Publication No. 2004/0167617 to Voellmicke et al., which is incorporated herein by this reference, describes an apparatus for mixing and retaining biological fluids. A manifold is used to deliver materials from two or more input syringes into a fluid retention chamber. However, an object of the Voellmicke et al. invention is "to provide a apparatus for mixing and retaining biological fluids comprising a manifold which minimizes intra-manifold mixing of the fluids." The manifolds do not facilitate, and in many cases minimize, intra-manifold mixing. There is again, among other things, the potential that the inputs will fail to mix or interact sufficiently.

SUMMARY

Embodiments of the present invention provide a mixing device for mixing a clotting agent with one or more input materials. The clotting agent and other inputs may flow or be caused to flow through a passageway having a mixer portion with a turbulent flow inducing shape. The mixing device may also have a body having a base for resting on a flat surface, a first input port on the body for receiving the clotting agent, a second input port on the body for receiving the input material, an output port on the body for removing a mixture of the clotting agent and the input material(s), with a passageway with a mixer portion through the body and connecting the first input port, the second input port, and the output port. Another embodiment is a method of mixing a clotting agent with one or more input materials. The method may involve passing the clotting agent and the input material through the mixer portion of a passageway.

STATEMENT OF THE INVENTION

According to a first aspect of the invention, there is provided:
    A mixing device comprising a passageway for mixing a clotting agent with an input material, a first container containing the clotting agent, a second container containing the input material, the containers in communication with the passageway, characterized in that a mixer portion of the passageway has a turbulent flow inducing shape.

According to a second aspect of the invention, there is provided:
    The above mixing device, in which there is further provided (a) a body comprising the passageway and a base for resting on a flat surface; (b) the first container containing the clotting agent in communication with the passageway at a first input port on the body; (c) the second container containing the input material in communication with the passageway at a second input port on the body; and (d) a receiving container in communication with the passageway at an output port on the body, for removing a mixture of the clotting agent and the input material; characterized in that
    the passageway through the body connects the first input port, the second input port, and the output port, and comprises the mixer portion with the turbulent flow inducing shape.

According to a third aspect of the invention, there is provided:
    A method of mixing a clotting agent with an input material, characterized in that the method comprises:
    providing a mixing device comprising a passageway, a first container of the clotting agent in communication with the passageway, and a second container of the input material in communication with the passageway; and
    passing the clotting agent and the input material at approximately the same time through a mixer portion of a passageway with a turbulent flow inducing shape.

According to a further aspect of the invention, there is provided:
    One of the mixing devices or methods above, in which the mixer portion comprises an hourglass-shaped tubular portion.

According to a further aspect of the invention, there is provided:
    One of the mixing devices or methods above, in which the mixer portion comprises a shape of repeating hourglasses.

According to a further aspect of the invention, there is provided:
    One of the mixing devices or methods above, in which the mixer portion comprises a first portion and a second portion, in which a diameter of the first portion is greater than a diameter of the second portion.

According to a further aspect of the invention, there is provided:
    One of the mixing devices or methods above, in which the mixer portion comprises a first portion, a second portion, and a third portion, in which a diameter of the first portion is greater than a diameter of the second portion and the diameter of the second portion is less than a diameter of the third portion.

According to a further aspect of the invention, there is provided:
    One of the mixing devices or methods above, in which the mixer portion comprises a tubular portion having a circular cross section.

According to a further aspect of the invention, there is provided:
    One of the mixing devices or methods above, in which the mixer portion comprises a tubular portion having a cross section shape that varies along a length of the portion.

According to a further aspect of the invention, there is provided:
    One of the mixing devices or methods above, in which the mixer portion comprises a first portion and a second portion, in which a width of the first portion is greater than a width of the second portion.

According to a further aspect of the invention, there is provided:
    One of the mixing devices or methods above, in which the mixer portion comprises a first portion, a second portion, and a third portion, in which a width of the first portion is greater than a width of the second portion and the width of the second portion is less than a width of the third portion.

According to a further aspect of the invention, there is provided:
    One of the mixing devices or methods above, in which the mixer portion comprises a first portion and a second portion, in which a cross sectional area of the first portion is greater than a cross sectional area of the second portion.

According to a further aspect of the invention, there is provided:
    One of the mixing devices or methods above, in which the mixer portion comprises a first portion, a second portion, and a third portion, in which a cross sectional area of the first portion is greater than a cross sectional area of the second portion and the cross sectional area of the second portion is less than a cross sectional area of the third portion.

According to a further aspect of the invention, there is provided:
    One of the mixing devices or methods above, in which the mixer comprises a first portion, a second portion, a third portion, and a fourth portion in which a cross sectional area of the first portion is greater than a cross sectional area of the second portion, the cross sectional area of the second portion is less than a cross sectional area of the third portion, and the cross sectional area of the third portion is greater than a cross sectional area of the fourth portion.

According to a further aspect of the invention, there is provided:
    One of the mixing devices or methods above, in which the clotting agent is thrombin.

According to a further aspect of the invention, there is provided:

One of the mixing devices or methods above, in which the mixer portion comprises a portion having a tortuous shape.

BRIEF DESCRIPTION OF FIGURES

FIGS. 5a-e are schematic views of alternative mixer portions of passageways according to several embodiments of the present invention.

FIGS. 6a-e are schematic views of alternative mixer portions of passageways according to several embodiments of the present invention.

FIG. 7 is a schematic view of a mixer portion of a passageway according to one embodiment of the present invention.

FIG. 8 is a schematic view of a mixer portion of a passageway according to one embodiment of the present invention.

DETAILED DESCRIPTION OF FIGURES

Introduction

Figure 1:
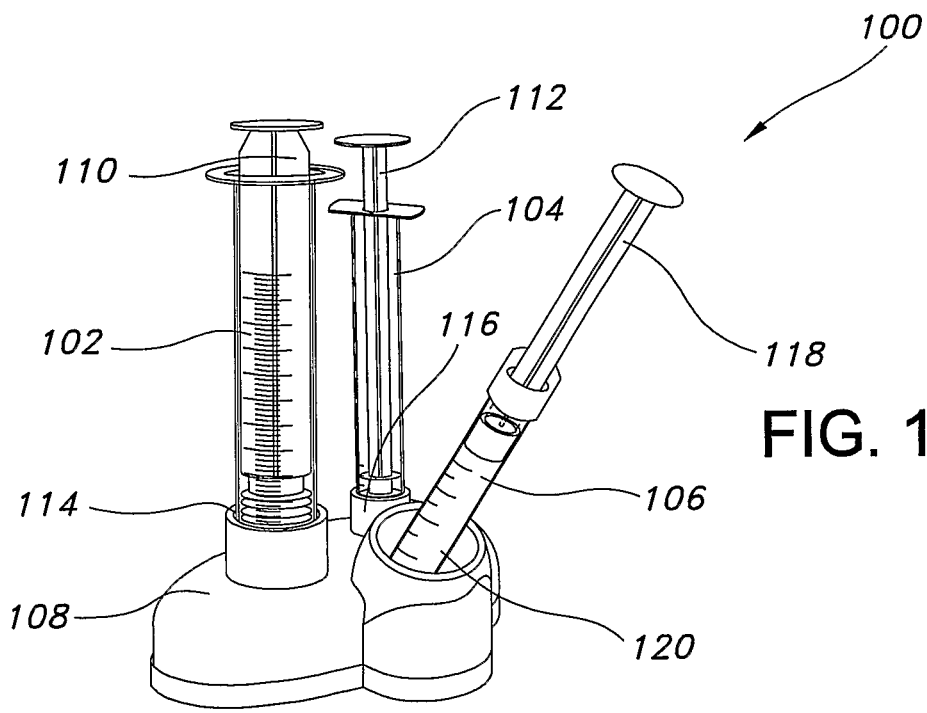
FIG. 1 is perspective view of a mixing device according to an embodiment of the present invention.

FIG. 1 shows a mixing device 100 according to one embodiment of the present invention. The mixing device 100 is used with a first input syringe 102, a second input syringe 104, and a receiving syringe 106. Alternative embodiments may substitute test tubes, bags, or other suitable containers for one or more of the syringes and may utilize other suitable methods, including gravity, to cause the inputs to flow. For convenience all such structures are included within the meaning of "syringes" or "containers" for purposes of this document. The base 108 of the mixing device 100, which may be a manifold, is preferably flat so that the mixing device can rest on a flat surface. The first input syringe 102 is controlled by plunger 110 and is connected to the mixing device 100 at port 114. The second input syringe 104 is controlled by plunger 112 and connected to the mixing device 100 at port 116. The receiving syringe 106 also has a plunger 118 and connects to the mixing device at a port 120. Preferably the receiving syringe 106 is angled with respect to the two input syringes 102, 104, which are preferably aligned parallel with and near to one another. Generally, the syringes 102, 104, 106 are attached to the base via Luer lock, slip fit, threading, or other suitable quick-fit mechanism.

The mixing device may be made from any hemocompatible material including but not limited to stainless steel, titanium, or other compatible metal, or suitable polymer. Various manufacturing methods or combinations thereof are appropriate including but not limited to compression molding, injection molding, lathe machining, mill machining, centers machining, cold forging and/or warm forging.

In use, a clotting agent is placed in one syringe 104 and one or more input materials are placed in the other input syringe 102. Some input material may also be placed in the receiving syringe 106, if desired. For example, bone graft may be placed in the receiving syringe 106. Input materials generally include but are not limited to constituents such as blood, blood derived product, platelet rich concentrate, bone marrow, bone marrow derived product, scaffolding substance, proteins, angiogenic factors, osteogenic factors, antibacterial agents, drugs, pain medication, and/or any other suitable medically beneficial input material. To mix the input material or materials with the clotting agent, the plungers 110, 112 on the input syringes 102, 104 are depressed to push the clotting agent and input material(s) through the body 108, where they mix together, and into the receiving syringe 106.

It should be noted that embodiments of the present invention involve mixing devices and methods that utilize any number of input materials from any number of input syringes or other containers. As examples, there may be a single input syringe for both the clotting agent and one input material. There may be an input syringe for the clotting agent and an input syringe for a first input material. There may be an input syringe for the clotting agent, an input syringe for a first and second input material, and an input syringe for a third input material. Any suitable combination of input syringes and input materials may be used. Likewise, any number of receiving syringes may also be used.

The Mixer potion of the Passageway

Figure 2A:
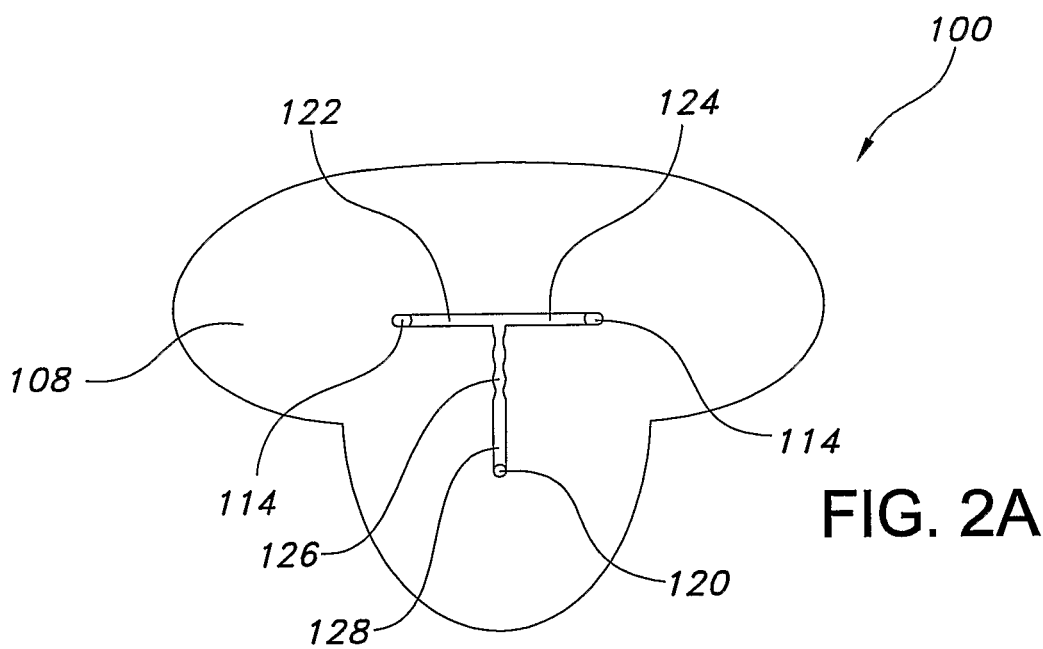
FIGS. 2a-b are schematic views showing the passageway and mixer portion of the passageway within the mixing device of FIG. 1.
Figure 2B:
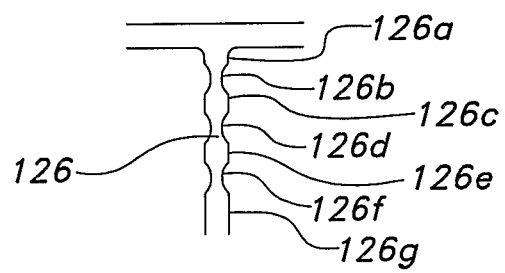

Referring now to FIGS. 2a-b, the first input port 114, second input port 116, and receiving port 120 are connected by intersecting passageways 122, 124, 126, 128, that together comprise a passageway connecting the three ports 114, 116, 120. A mixer portion 126 of the passageway has a geometry or shape that induces turbulent flow of fluid flowing through it. When the clotting agent and other input material(s) are injected into the body of the mixing device 100, they mix together within the passageway and the mixture is pushed into the output or receiving syringe 106. Mixing occurs because a portion of the passageway through the mixing device has a geometry or shape that facilitates mixing of the clotting agent and input material(s). In many cases, the mixture pushed into the receiving syringe will be sufficiently mixed such that no shaking is required. The thorough mixing of the input materials helps ensure that the resulting mixture will be sufficiently congealed.

The internal geometry or shape of at least a portion 126 of the passageway through the mixing device 100 causes turbulent flow of fluid passing through the passageway. In some embodiments, the shape of a mixer portion 126 of the passageway creates differences in velocity and/or local pressure in the fluid flowing through the passageway. The areas of different pressures and/or velocities lead to turbulence. A portion 126 of the passageway can be shaped to affect changes in velocity of fluids, pressure, or both, as well as other factors that contribute to turbulence and mixing of the fluid. Note that the changes in velocity can be with respect to the magnitude and/or direction of the fluid velocity.

In the embodiment shown in FIGS. 2a-b, the mixer portion 126 has a repeating hourglass shape that induces turbulent flow upon fluid moving through. The hourglass-shaped mixer portion 126 has a generally tubular shape with varying diameters along its length. The diameter of the mixer portion 126 decreases from first portion 126a to second portion 126b, increases to third portion 126c, decreases again to fourth portion 126d, increases again to fifth portion 126e, decreases again to sixth portion 126f, and increases again to seventh portion 126g.

Input Syringe Diameter

The ratio of input material to clotting agent to other input materials in the resulting mixture can be selected by the appropriate selection of input syringes. For example, the ratio can be selected by selecting input syringes have certain diameters. As a specific example, a configuration of a tubular input syringe used for Thrombin having a diameter one third of diameter of a tubular input syringe used for platelet concentrate would yield a thrombin/platelet concentrate ratio in the resulting mixture of 1:9, assuming that all of the Thrombin and platelet concentrate passes into the mixture. In practice, some of the Thrombin and/or platelet concentrate could remain in the input syringes and/or passageway. Accordingly, for a desired resulting mixture ratio, a more precise ratio may be determined by simple testing. In most cases, the strength of the clotting agent will be such that the ratio simple needs to be above a certain value to ensure sufficient clotting. For example, because of the potency of Thrombin as a clotting agent, in most cases a ratio of 1:10 will provide more than enough clotting agent with enough margin of error that mixing of all the clotting agent with all of the input material need not occur.

The variations of the diameter of the mixer portion 126 may cause fluid flowing through the mixer portion 126 to have areas of relatively high and low pressure and/or areas of relatively high and low velocity. These differences in velocity and pressure may contribute to turbulence in the fluid flowing through the mixer 126, which may help the fluid to mix.

Input Plunger Coordination

The fluid may, and preferably does, contain some of the input material(s) from the first input syringe 102 some of the clotting agent from the second input syringe 104 and. As the fluid is mixed by the turbulence created by the shape of the mixer portion 126 of the passageway, the clotting agent and input material(s) are mixed together. To help ensure that the fluid flowing into the mixer portion has some material from each of the input syringes 102, 104, the injection from the input syringes 102, 104 is preferably coordinated to occur at or around the same time. Depressing the plungers 110, 112 of the input syringes 102, 104 at or around the same time helps ensure that the fluid entering the mixer portion 126 has some of both inputs.

Figure 3:
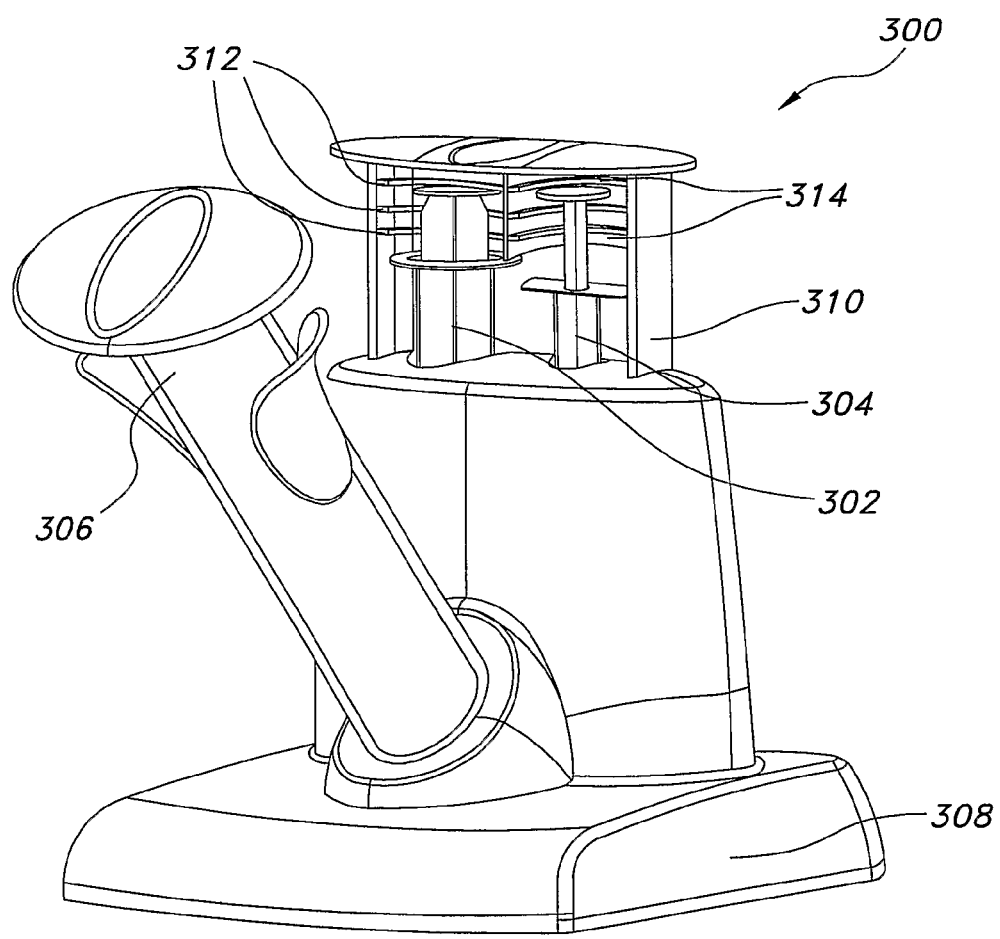
FIG. 3 is a perspective view of a mixing device according to another embodiment of the present invention.
Figure 4:
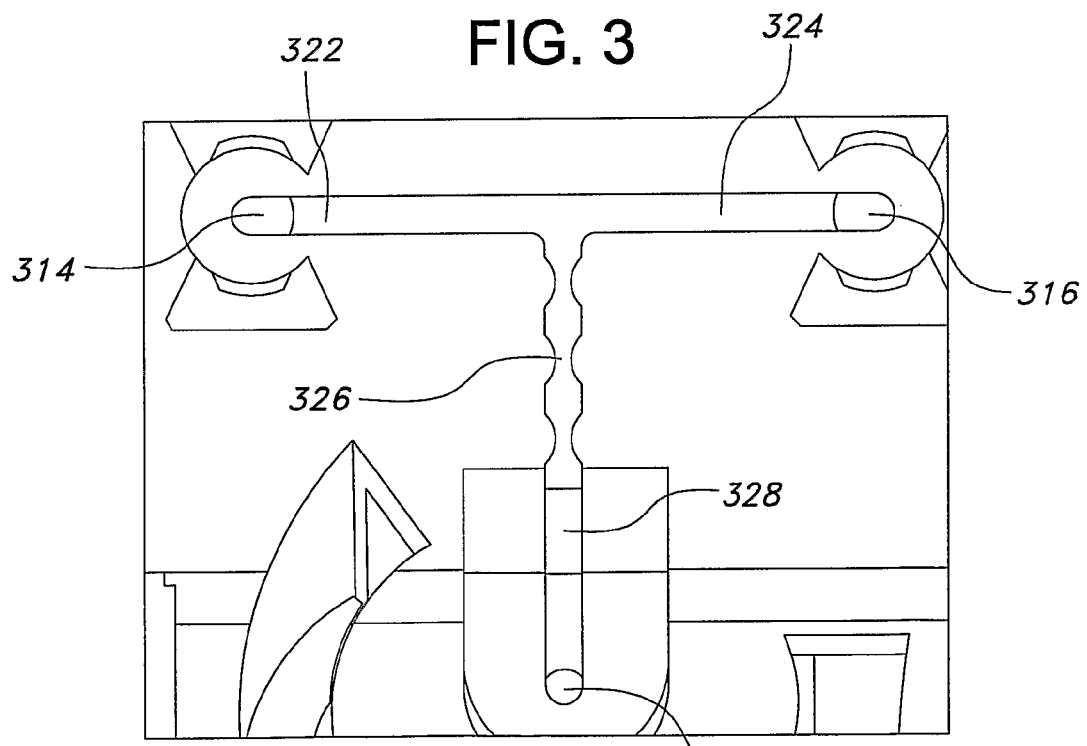
FIG. 4 is a schematic view showing the passageway and mixer portion of passageway within the mixing device of FIG. 3.

FIGS. 3 and 4 illustrate a mixing device 300 according to another embodiment of the present invention. This device 300 uses two input syringes 302, 304, and a receiving syringe 306 and has a base 308. A handle 310 is used to ensure that the plungers on the two input syringes 202 and 204 are depressed at the same time and rate. The handle 310 covers the plungers of the two input syringes 202, 204. Attachment member 312, 314 on the inside of the handle 310 may attach to or otherwise contact the syringe plungers so that syringe plunger movement is controlled by the movement of the handle 310. This contact may be secure or may have some extra room for one or more of the input syringe plunger. For example, one of the syringes could be secured such that its movement does not occur until the handle has moved ¼ inch, while the other syringe is secured such that it begins to move immediately upon movement of the handle. Virtually any suitable attaching, securing or connecting technique between handle and plunger may be used. Alternatively, the plungers could be molded together or otherwise attached to one another or to a connector to ensure that the timing of depression of the input syringe plungers is coordinated in the desired manner.

FIG. 4 shows the internal passageway of the mixing device of FIG. 3. A first input port 314, second input port 316, and receiving port 320 are connected by intersecting passageways 322, 324, 326, 328, that together comprise a passageway connecting the three ports 314, 316, 320. The mixer portion 326 of the passageway has a turbulent flow inducing geometry or shape.

Turbulent Flow Inducing Shape

The turbulent flow in the mixer portion 326 contributes to the mixing and dispersion of the molecules of the clotting agent and input material(s) within the fluid flowing through the passageway and into the receiving syringe 306. Turbulent flow is a form of fluid flow in which particles of the fluid move with irregular local velocities, pressures, and/or other fluid characteristics, as described herein and otherwise known to those of skill in the art. Note that irregularities in velocity may be with respect to the magnitude and/or the direction of the fluid flow.

The mixer or mixer portion of the passageway of the present invention can have a variety of different shapes or geometries that induce turbulent flow. For example, the cross section of the mixer portion of certain embodiments is circular while the cross section in other embodiments is not circular. Various geometric shapes could be used to create the pressure and velocity differences, including but not limited to regular and irregular polygons, circles, ellipses, spheres, ellipsoids, wave forms, etc. These mixing mechanisms can be used alone or in combination with others or repeated as necessary with or without staging volumes between mixing mechanisms. FIGS. 5-8 provide some examples of exemplary geometric two and three-dimensional shapes, or combinations thereof, used in alternative embodiments of the mixer portion of the passageway, having turbulent flow inducing shapes.

FIGS. 5a-e illustrate alternative shapes for a mixer portion having a turbulent flow inducing shape. In these embodiments, the shape shown may be implemented in two dimensions (rectangular cross section) or three dimensions (circular cross section), or a combination of two and three dimensions. Generally, for these embodiments, the diameter or width of the shape changes along the length of the mixer portion of the passageway. Accordingly, fluid flowing though such mixer portions would experience turbulence in the form of at least irregular pressures, which may create irregular velocities and cause the fluid components to intermix.

FIGS. 6a-e also illustrate alternative shapes for a mixer portion having a turbulent flow inducing shape. Also for these embodiments, the shape shown may be implemented in two or three dimensions, or a combination. For these embodiments, the direction of fluid flow is manipulated by the shape of the mixer portion of the passageway. The tortuous paths induce turbulence. Fluid flowing though such mixer portions experience turbulence in the form of at least irregular directional velocities, which may cause the fluid components to intermix.

FIGS. 7 and 8 are combinations of different mixing shapes. In FIG. 7, the different mixing shapes occur sequentially along the length of the mixer portion of the passageway. Fluid could be caused to flow in either direction through a mixing portion having the shape depicted in FIG. 7.

In FIG. 8, different mixing shapes are combined together along the mixing chamber to create a blended shape that produced irregularities of pressure and velocity of fluid flowing through.

Additional combinations of suitable shapes may also be used. The creation of turbulence within the passageway of the mixing device is not limited to the particular embodiments described herein. The fluid may be affected in a variety of suitable manners and combination of manners.

Other Turbulent Flow Inducing Factors and Mechanisms

Turbulence within the passageway of the mixing device can be created using a variety of other suitable mechanisms. For example, turbulence could be created by an electrically powered shaker within the mixing device that vibrates the passageway through which the fluid flows. As another example, turbulence could be created by spinning or rotating the passageway through which the fluid flows. As yet another example, the passageway could contain a rotating mixer component that stirs or otherwise disturbs the fluid flowing through the passageway.

Turbulent flow may also be caused or enhanced by a variety of factors including the relative viscosity of the clotting agent and input material(s), the speed at which the input plungers are depressed, environmental factors, etc. Accordingly, turbulence may affected by mechanisms that affect pressure, velocity, change in pressure, acceleration, static velocity, dynamic velocity, kinematic velocity, density, inertial force and other elements of the Navier Stokes equations. A particular turbulence inducing mechanism may be appropriate to facilitate mixing of one combination of clotting agent with certain input material(s) while another mechanism is appropriate for another combination.

In general, some embodiments of the invention have the advantage of mixing the constituent input materials within a mixing device to ensure substantially even, repeatable mixing, while eliminating the need to shake or agitate the receiving syringe containing the mixture.

Modifications, additions and deletions may be made to the embodiments described above and shown in the accompanying figures without departing from the scope or spirit of the present invention. For example, while the devices and methods described primarily relate to manually controlled and operated mixing devices, the invention may also be utilized in a semi or fully-automated mixing device. As another example, the mixing device can be made of any biocompatible material (plastic, metal, etc.), may itself define the passageway and mixer portion, and/or may have internal tubing or other plumbing that defines the passageway and mixer portion. As yet another example, while the invention described is primarily for single use applications, it could be used with appropriate cleaning and sterilization items that facilitate multiple uses of the device. In addition, the devices and methods described here are intended to mix a variety of known and unknown inputs. The invention is not limited to any particular inputs or input characteristics.

The invention claimed is:

1. A mixing device comprising
a body comprising:
    a passageway that connects a first input port attaching a first container, a second input port attaching a second container, and an output port attaching a receiving container; and
    a base configured to rest on top of a flat surface such that the first input port, the second input port, and the output port extend generally upwardly, the passageway for mixing a clotting agent with an input material, the first container containing the clotting agent, the second container containing the input material, and the receiving container for receiving a mixture of the clotting agent and the input material,
    wherein a mixer portion of the passageway has a turbulent flow inducing shape; and
    wherein a diameter of the first container differs from a diameter of the second container, wherein a ratio of the diameter of the first container to the diameter of the second container controls a ratio of the clotting agent to the input material in the mixture that is mixed by the mixing device.

2. The mixing device of claim 1, in which the mixer portion comprises an hourglass-shaped tubular portion.

3. The mixing device of claim 1, in which the mixer portion comprises a shape of repeating hourglasses.

4. The mixing device of claim 1, in which the mixer portion comprises a first portion and a second portion, in which a diameter of the first portion is greater than a diameter of the second portion.

5. The mixing device of claim 1, in which the mixer portion comprises a tubular portion having a circular cross section.

6. The mixing device of claim 1, in which the mixer portion comprises a tubular portion having a cross section shape that varies along a length of the portion.

7. The mixing device of claim 1, in which the mixer portion comprises a first portion and a second portion, in which a width of the first portion is greater than a width of the second portion.

8. The mixing device of claim 1, in which the mixer portion comprises a first portion, a second portion, and a third portion, in which a width of the first portion is greater than a width of the second portion and the width of the second portion is less than a width of the third portion.

9. The mixing device of claim 1, in which the mixer portion comprises a first portion and a second portion, in which a cross sectional area of the first portion is greater than a cross sectional area of the second portion.

10. The mixing device of claim 1, in which the mixer portion comprises a first portion, a second portion, and a third portion, in which a cross sectional area of the first portion is greater than a cross sectional area of the second portion and the cross sectional area of the second portion is less than a cross sectional area of the third portion.

11. The mixing device of claim 1, in which the mixer comprises a first portion, a second portion, a third portion, and a fourth portion in which a cross sectional area of the first portion is greater than a cross sectional area of the second portion, the cross sectional area of the second portion is less than a cross sectional area of the third portion, and the cross sectional area of the third portion is greater than a cross sectional area of the fourth portion.

12. The mixing device of claim 1, in which the mixer portion comprises a portion having a tortuous shape.

13. The mixing device of claim 1, in which the mixer portion comprises a first portion, a second portion, and a third portion, in which a diameter of the first portion is greater than a diameter of the second portion and the diameter of the second portion is less than a diameter of the third portion.

14. A mixing device comprising
a body comprising:
    a passageway that connects a first input port attaching a first syringe, a second input port attaching a second syringe, and an output port attaching a receiving syringe; and
    a base configured to rest on a flat surface such that the first input port, the second input port, and the output port extend generally upwardly, the passageway for mixing a clotting agent with an input material, the first syringe containing the clotting agent, the second syringe containing the input material, and the receiving syringe for receiving a mixture of the clotting agent and the input material,
    wherein a mixer portion of the passageway has a turbulent flow inducing shape; and
    wherein the mixing device is configured to ensure that the first input syringe and the second input syringe are depressed at the same rate.

15. The mixing device of claim 14 wherein a handle ensures that the first input syringe and the second input syringe are depressed at the same rate.

16. The mixing device of claim 15 wherein the handle covers both a plunger of the first input syringe and a plunger of a second input syringe.

17. The mixing device of claim 15 wherein the handle ensures that the first input syringe and the second input syringe are depressed at the same time.

18. The mixing device of claim 14 wherein the first input syringe and the second input syringe are attached to one another to ensure that the first input syringe and the second input syringe are depressed at the same rate.

19. The mixing device of claim 14 the first input syringe and the second input syringe are molded together.

20. A mixing device comprising
a body comprising:
    a passageway that connects a first input port attaching a first syringe, a second input port attaching a second syringe, and an output port attaching a receiving syringe; and
    a base configured to rest on a flat surface such that the first input port, the second input port, and the output port extend generally upwardly, the passageway for mixing a clotting agent with an input material, the first syringe containing the clotting agent, the second syringe containing the input material, and the receiving syringe for receiving a mixture of the clotting agent and the input material,
wherein a mixer portion of the passageway has a turbulent flow inducing shape;
wherein the mixing device is configured to ensure that the first input syringe and the second input syringe are depressed at the same rate; and
wherein a diameter of the first syringe differs from a diameter of the second syringe, wherein a ratio of the diameter of the first syringe to the diameter of the second syringe controls a ratio of the clotting agent to the input material in a mixture that is mixed by the mixing device.

* * * * *